(12) United States Patent
Kumta et al.

(10) Patent No.: US 11,638,645 B2
(45) Date of Patent: May 2, 2023

(54) BIOMIMETIC PLYWOOD MOTIFS FOR BONE TISSUE ENGINEERING

(71) Applicant: UNIVERSITY OF PITTSBURGH—OF THE COMMONWEALTH SYSTEM OF HIGHER EDUCATION, Pittsburgh, PA (US)

(72) Inventors: Prashant N. Kumta, Pittsburgh, PA (US); Gary Yu, Pittsburgh, PA (US); Abhijit Roy, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 274 days.

(21) Appl. No.: 17/027,810

(22) Filed: Sep. 22, 2020

(65) Prior Publication Data
US 2021/0000602 A1 Jan. 7, 2021

Related U.S. Application Data

(63) Continuation-in-part of application No. 16/099,459, filed as application No. PCT/US2017/033480 on May 19, 2017, now Pat. No. 10,806,586.
(Continued)

(51) Int. Cl.
*A61F 2/30* (2006.01)
*A61F 2/28* (2006.01)
(Continued)

(52) U.S. Cl.
CPC .............. *A61F 2/28* (2013.01); *A61F 2/3094* (2013.01); *B33Y 10/00* (2014.12); *B33Y 80/00* (2014.12);
(Continued)

(58) Field of Classification Search
CPC ................ A61F 2/28; A61F 2002/2817; A61F 2002/2835; A61F 2002/2839;
(Continued)

(56) References Cited

U.S. PATENT DOCUMENTS 5,064,439 A 11/1991 Chang et al.
5,181,930 A 1/1993 Dumbleton et al.
(Continued)

OTHER PUBLICATIONS

Giraud Guille et al., Bone Matrix Like Assemblies of Collagen: Frrom Liquid Crystals to Gels and Biomimetic Materials, Micron 36 (2005), pp. 602-608.
(Continued)

*Primary Examiner* — Alvin J Stewart
(74) *Attorney, Agent, or Firm* — Carol A. Marmo; Eckert Seamans Cherin & Mellott, LLC

(57) ABSTRACT

The invention relates generally to generation of biomimetic scaffolds for bone tissue engineering and, more particularly, to multi-level lamellar structures having rotated or alternated plywood designs to mimic natural bone tissue. The invention also includes methods of preparing and applying the scaffolds to treat bone tissue defects. The biomimetic scaffold includes a lamellar structure having multiple lamellae and each lamella has a plurality of layers stacked parallel to one another. The lamellae and/or the plurality of layers is rotated at varying angles based on the design parameters from specific tissue structural imaging data of natural bone tissue, to achieve an overall trend in orientation to mimic the rotated lamellar plywood structure of the naturally occurring bone tissue.

11 Claims, 12 Drawing Sheets

Related U.S. Application Data

(60) Provisional application No. 62/338,790, filed on May 19, 2016.

(51) Int. Cl.
  *B33Y 10/00* (2015.01)
  *B33Y 80/00* (2015.01)
  *B29C 64/165* (2017.01)

(52) U.S. Cl.
  CPC .............. *A61F 2002/2835* (2013.01); *A61F 2002/30062* (2013.01); *A61F 2002/30224* (2013.01); *A61F 2002/30973* (2013.01); *A61F 2002/30985* (2013.01); *A61F 2310/00005* (2013.01); *A61F 2310/00017* (2013.01); *A61F 2310/00023* (2013.01); *A61F 2310/00029* (2013.01); *A61F 2310/00041* (2013.01); *A61F 2310/00293* (2013.01); *B29C 64/165* (2017.08)

(58) Field of Classification Search
  CPC ........ A61F 2/30942; A61F 2002/30948; A61F 2002/30971; A61F 2002/30962; A61F 2002/30985
  See application file for complete search history.

(56) References Cited

U.S. PATENT DOCUMENTS

| | | | |
|---|---|---|---|
| 5,192,330 A | 3/1993 | Chang et al. | |
| 5,876,452 A | 3/1999 | Athanasiou et al. | |
| 6,193,755 B1 | 2/2001 | Metz-Stavenhagen et al. | |
| 6,193,756 B1 | 2/2001 | Studer et al. | |
| 6,206,924 B1 | 3/2001 | Timm | |
| 6,283,997 B1 | 9/2001 | Garg et al. | |
| 6,454,811 B1* | 9/2002 | Sherwood | A61F 2/28 623/23.72 |
| 7,353,153 B2* | 4/2008 | Ascenzi | B33Y 50/00 703/2 |
| 7,799,077 B2* | 9/2010 | Lang | A61F 2/4261 606/86 R |
| 8,337,507 B2* | 12/2012 | Lang | G06K 9/00 606/86 R |
| 8,414,654 B1 | 4/2013 | Ganey | |
| 8,702,808 B2* | 4/2014 | Teoh | A61L 27/46 623/23.61 |
| 9,370,426 B2 | 6/2016 | Gabbrielli et al. | |
| 9,549,823 B2 | 1/2017 | Hunt et al. | |
| 9,925,046 B2* | 3/2018 | Larsen | A61F 2/30907 |
| 10,022,233 B1 | 7/2018 | Gall et al. | |
| 10,478,312 B2 | 11/2019 | Mcshane, III et al. | |
| 10,667,924 B2 | 6/2020 | Nyahay et al. | |
| 10,675,158 B2 | 6/2020 | Unger et al. | |
| 10,876,095 B1* | 12/2020 | Hofmeister | A61L 15/44 |
| 2002/0188347 A1* | 12/2002 | Mathis | A61F 2/915 623/1.19 |
| 2003/0036800 A1* | 2/2003 | Meredith | A61L 27/3683 623/23.63 |
| 2003/0065400 A1* | 4/2003 | Beam | C04B 35/638 623/23.51 |
| 2003/0114936 A1 | 6/2003 | Sherwood et al. | |
| 2003/0232071 A1* | 12/2003 | Gower | A61L 27/24 424/443 |
| 2004/0005297 A1* | 1/2004 | Connelly | A61L 27/3891 435/366 |
| 2004/0249463 A1 | 12/2004 | Bindseil et al. | |
| 2005/0015154 A1 | 1/2005 | Lindsey et al. | |
| 2005/0112397 A1 | 5/2005 | Rolfe et al. | |
| 2005/0131662 A1 | 6/2005 | Ascenzi et al. | |
| 2007/0116734 A1 | 5/2007 | Akash | |
| 2007/0179610 A1 | 8/2007 | Biedermann et al. | |
| 2007/0181239 A1 | 8/2007 | Yamazawa et al. | |
| 2007/0203584 A1* | 8/2007 | Bandyopadhyay | B22F 3/105 623/901 |
| 2008/0147187 A1 | 6/2008 | Bollinger et al. | |
| 2010/0234955 A1* | 9/2010 | Santerre | A61L 27/3856 523/113 |
| 2010/0291401 A1* | 11/2010 | Medina | B22F 3/115 219/121.66 |
| 2010/0310623 A1 | 12/2010 | Laurencin et al. | |
| 2010/0331998 A1* | 12/2010 | Ringeisen | A61L 27/52 623/23.61 |
| 2011/0313538 A1 | 12/2011 | Oh et al. | |
| 2012/0064288 A1 | 3/2012 | Makano et al. | |
| 2012/0150299 A1 | 6/2012 | Ergun et al. | |
| 2013/0006354 A1 | 6/2013 | Pressacco | |
| 2013/0218282 A1 | 8/2013 | Hunt | |
| 2013/0331893 A1 | 12/2013 | Shih | |
| 2014/0010951 A1 | 1/2014 | Margas et al. | |
| 2014/0236299 A1 | 8/2014 | Roeder et al. | |
| 2014/0242140 A1* | 8/2014 | Neu | A61K 38/39 514/16.7 |
| 2014/0371863 A1 | 12/2014 | Vanasse et al. | |
| 2015/0150681 A1 | 6/2015 | Ricci et al. | |
| 2015/0238318 A1 | 8/2015 | Mccullen | |
| 2015/0289979 A1 | 10/2015 | Gabele et al. | |
| 2015/0297349 A1 | 10/2015 | Butscher et al. | |
| 2016/0081809 A1 | 3/2016 | Schneider et al. | |
| 2016/0106540 A1* | 4/2016 | Kuntz | A61F 2/2846 264/44 |
| 2016/0113695 A1 | 4/2016 | Globerman et al. | |
| 2016/0242831 A1 | 8/2016 | Durkin et al. | |
| 2016/0262894 A1* | 9/2016 | Cronstein | A61F 2/28 |
| 2016/0271296 A1 | 9/2016 | Jongpaiboonkit et al. | |
| 2017/0181785 A1 | 6/2017 | Beyar et al. | |
| 2017/0216033 A1 | 8/2017 | Daniel et al. | |
| 2017/0231767 A1* | 8/2017 | Larsen | A61F 2/2846 623/23.58 |
| 2017/0354503 A1 | 12/2017 | Larsen et al. | |
| 2018/0221153 A1 | 8/2018 | Daniel et al. | |
| 2019/0030212 A1* | 1/2019 | Zhang | A61L 27/52 |
| 2019/0167433 A1 | 6/2019 | Allen et al. | |
| 2019/0240036 A1 | 8/2019 | Kowalczyk et al. | |
| 2019/0350715 A1 | 11/2019 | Liu et al. | |
| 2020/0030102 A1* | 1/2020 | Mullens | A61F 2/30907 |
| 2020/0179560 A1 | 6/2020 | Durkin et al. | |
| 2021/0212834 A1* | 7/2021 | Karl | A61F 2/3609 |
| 2021/0298908 A1* | 9/2021 | Holmes | A61F 2/30756 |

OTHER PUBLICATIONS

Seitz et al., Three-Dimensional Printing of Porous Ceramic Scaffolds for Bone Tissue Engineering, Wiley Interscience (Jun. 24, 2005), pp. 782 & 785.

* cited by examiner

BIOMIMETIC PLYWOOD MOTIFS FOR BONE TISSUE ENGINEERING

CROSS-REFERENCE TO RELATED APPLICATIONS

This application is a continuation-in-part application, which claims the priority of and benefit from U.S. Ser. No. 16/099,459 entitled "BIOMIMETIC PLYWOOD MOTIFS FOR BONE TISSUE ENGINEERING," filed on Nov. 7, 2018, which is a U.S. National Stage Application under 35 U.S.C. § 371 of PCT International Application No. PCT/US2017/033480, entitled "BIOMIMETIC PLYWOOD MOTIFS FOR BONE TISSUE ENGINEERING," filed on May 19, 2017, which claims priority under 35 U.S.C. § 119(e) from U.S. provisional patent application No. 62/338,790, entitled "BIOMIMETIC ROTATED LAMELLAR PLYWOOD MOTIFS OF METAL ALLOY SCAFFOLDS BY ADDITIVE MANUFACTURING FOR BONE TISSUE ENGINEERING," filed on May 19, 2016, the contents of which are incorporated herein by reference.

GOVERNMENT SUPPORT

This invention was made with government support under GM008208 awarded by the National Institutes of Health (NIH) and FA8650-12-2-7230 awarded by the Air Force Research Laboratory (AFRL). The government has certain rights in the invention.

FIELD OF THE INVENTION

The invention relates generally to scaffolds for bone tissue engineering and, more particularly, to multi-level lamellar structures having rotated or alternated plywood designs to mimic natural bone tissue. The invention also includes methods of preparing and applying the scaffolds to treat bone tissue defects.

BACKGROUND

The treatment of critical sized segmental bone defects resulting from traumatic fractures through a space-filling, load-bearing bone graft substitute is an area of increasing interest in the development of orthopedic implants. Traditional methods of treatment include autologous or allogenic, as well as, synthetic bone grafts. While fulfilling criteria of osteoconductivity (surface biocompatibility for growth of bone tissue) and osteoinductivity (recruitment and stimulation of immature cells into preosteoblasts), these methods have associated therewith risks of complications and they are highly invasive. The synthesis and design of synthetic bone scaffolds addresses the known disadvantages of bone grafts. Thus, the treatment of large-scale bone defects and the development of sophisticated synthetic tissue substitutes are currently major issues aggressively researched in the field of bone tissue engineering.

Layer-by-layer or solid free-form fabrication (SFF) approaches for porous bone scaffolds have been shown to be capable of producing patient specific complex 3-D structures generated from patient imaging modalities and computer-assisted design (CAD) models. More specifically, binder-jet 3-D printing (3-DP) methods can selectively deposit a liquid binder solution onto a bed of spread powder of varying homogeneous or inhomogeneous morphology to construct a CAD model on a layer-by-layer basis, e.g. additive manufacturing (AM). This technique features versatility in materials compositions using a wide range of powders and binder formulations, including metal alloys relevant to load-bearing orthopedic and craniofacial implants, such as, titanium, Co—Cr and Fe-based alloys.

The impact of structural design on mechanical performance of SFF scaffolds has been a subject of increasing interest in the field of materials science. Especially relevant to the field of orthopedic implant design, titanium, Co—Cr alloys, and titanium alloy scaffolds have been fabricated in geometric matrix designs. Similarly, bioceramic polymer and polymer composite scaffolds have also been explored for understanding structure-performance relationships, but most fabricated scaffold designs remain relatively unsophisticated in terms of geometric organization and its relationship to both mechanical and potential physiological performance. Previous research has commonly relied upon randomly arranged porous or a standardized orthogonal porous mesh design for simplicity in exploring compositional variations.

While mechanical performance has been a driving factor in the exploration of material alternatives for orthopedic load-bearing SFF applications, several studies have emphasized the significance of structural organization on mechanical performance in natural bone tissue. The concept of biomimetic design itself has been explored on a variety of size regimes for bone tissue engineering (BTE) given the complex hierarchical nature of bone structure.

Although past research has been successful in demonstrating significant differences in mechanical performance in relation to scaffold design, replication of complex behaviors of native tissue through biomimetic design is a direction requiring further consideration and effort. Thus, there is a need in the art to explore structure-based variations in mechanical performance of a simplified cylindrical lamellar scaffold featuring a biomimetic rotated or alternated plywood organization, with accompanying material and biological characterization, to design and develop a new level of biomimetic complexity in design, and demonstrate the fabrication capacities of binder-jet three dimensional printing (3-DP). Additive manufacturing, with its unique capacity to create complex architectures in a wide range of materials, presents opportunities to exploit a structurally biomimetic approach to designing and developing novel scaffolds with architectures mimicking the natural bone tissue, thus exhibiting improved mechanical performance.

SUMMARY OF THE INVENTION

In one aspect, the invention provides a biomimetic scaffold that includes a material selected from the group consisting of metal, metal alloy, polymer, ceramic and blends thereof; and a lamellar structure that includes a plurality of lamellae, each of the plurality of lamellae including a plurality of layers stacked parallel to one another. One or more of the plurality of lamellae and/or one or more of the plurality of layers is rotated at varying angles based on design parameters derived from specific tissue structural imaging data of natural bone tissue, to achieve an overall trend in orientation. The overall trend of the plurality of lamellae and/or the layers mimics a rotated lamellar plywood structure of the natural bone tissue and orientation of lamella therein.

The material can exhibit one or more properties selected from degradable, non-degradable, bioresorbable, non-bioresorbable, bioabsorbable, non-bioabsorbable, biocompatible, bioinert, bioactive and combinations thereof.

The plurality of layers can include sequential multiple layers of a given geometry. In certain embodiments, the scaffold has the shape of a cylinder and the plurality of layers include sequential, multiple concentric rings.

Each of the plurality of layers being rotated can have an angular rotation from 0 degrees to 90 degrees measured from a longitudinal axis of the scaffold.

The overall trend in the orientation of the plurality of layers in the scaffold can be a spiral twist with varying degree of control of the spiral pitch.

In certain embodiments, each of the plurality of layers can have an alternating mesh pattern.

The scaffold can be used in various applications, such as, an implantation device including a scaffold for implantation in a patient to treat bone tissue defects.

In another aspect, the invention provides a method of preparing a biomimetic scaffold. The method includes selecting a natural bone tissue specimen to mimic having a rotated plywood lamellar structure; performing structural imaging analysis of the natural bone tissue; employing data from the structural imaging analysis of bone to specify design parameters of the biomimetic scaffold and to determine angular displacement of lamella in the rotated plywood lamellar structure; obtaining a material composition for the scaffold, which is selected from metal, metal alloy, polymer, ceramic, and composites and blends thereof; forming the material composition into a plurality of layers; employing an additive process for forming, stacking and aligning the plurality of layers; and rotating one or more of the plurality of layers at varying rotational pitch to achieve an overall trend that mimics the angular displacement of lamella in the rotated plywood lamellar structure mimicking that of the natural bone tissue.

As previously described, the material can exhibit one or more properties selected from degradable, non-degradable, bioresorbable, non-bioresorbable, bioabsorbable, non-bioabsorbable, biocompatible, bioinert and bioactive.

The structural analysis can be selected from various imaging modalities that are known in the art, such as, micro-diffraction image analysis, polarized light microscopy, SEM surface tomography, X-ray diffraction, X-ray diffraction tomography, confocal microscopy and X-ray micro computed tomography and the like. The structural analysis can be employed to obtain specific and detailed information regarding the structural framework and construction of the natural material to be modeled in the biomimetic design.

Further, the additive process can be selected from conventional solid free-form and layered manufacturing processes, such as, 3-D printing, as well as, fused deposition modeling (FDM), laser beam and electron beam processes. The 3-D printing process can include use of a binder-jet-3-DP apparatus.

DETAILED DESCRIPTION OF THE PREFERRED EMBODIMENTS

Figure 1A:
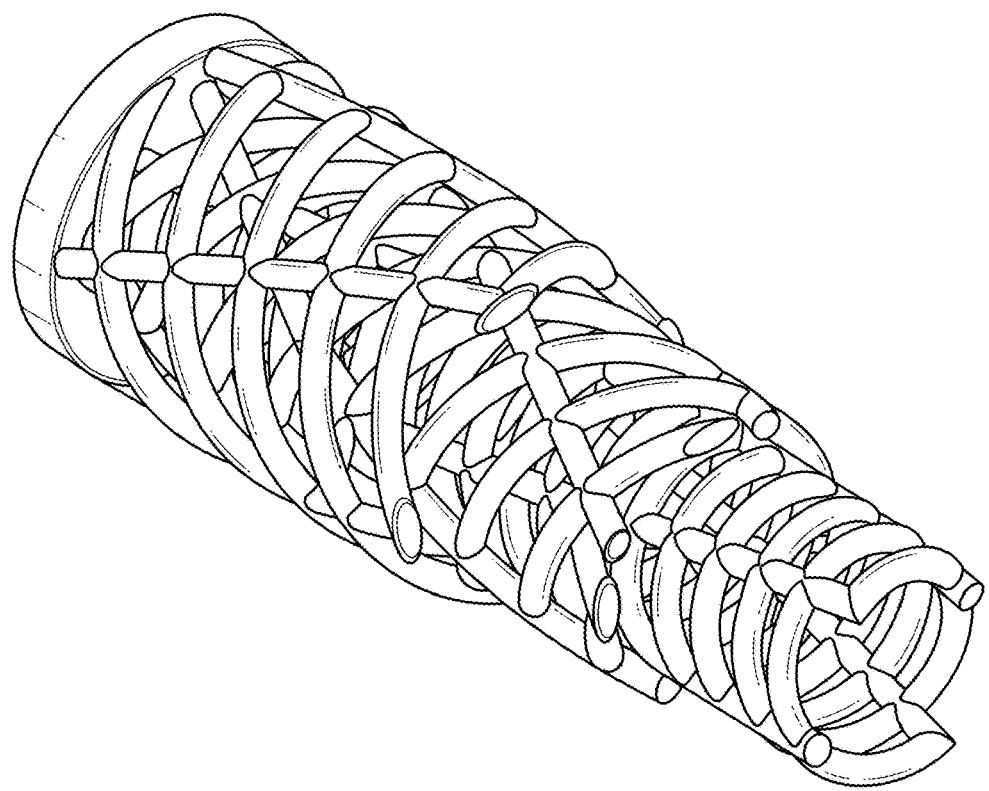
FIGS. 1(a) and 1(b) are CAD 3D images of scaffolds in accordance with certain embodiments of the invention, wherein 1(a) shows an alternating mesh design and 1(b) shows an orthogonal mesh design.

The present invention includes novel structural designs for additive manufactured tissue engineering scaffolds developed using a biomimetic design including plywood motifs of bone tissue that are rotated to various angular degrees or alternated to mimic or replicate the structural features and hierarchical architecture of natural bone tissue, and to demonstrate the improved mechanical performance and response under loads that are indicative of natural bone tissues. The invention provides for a biomimetic approach in designing the rotated or alternated plywood lamellar structure elucidated from natural bone tissue structural analysis in the context of an additively manufactured, a layered-by-layered, alloy scaffold for the purpose of tissue engineering applications.

There has been found a prominent motif of lamellar plywood organization in natural bone tissue, where subsequent layers or sheets, e.g., lamellae, of parallel mineral-embedded microfibers are rotated or alternated, at various angular degrees, to create an overall spiral twist with varying pitch, which then organize into cylindrical units referred to as osteons in the naturally occurring bone tissue. Mechanical properties, including extensibility, flexibility, stiffness in tension, compression and shear, load-bearing, and energy dissipating capacity against fracture crack propagation, are derived from the variations in the microfiber lamellar angle of this plywood motif. The variations in angularity between the layers/lamellae and/or across each layer/lamella, are highly relevant to the design and performance of a functional biomimetic orthopedic scaffold, which may also affect the extent of cellular infiltration occurring during the tissue regenerative process.

Without intending to be bound by any particular theory, it is believed synthetic scaffolds that mimic the variations in angularity of layers found in natural bone, will also mimic the mechanical properties that are exhibited by the natural bone. Thus, it is an objective of the invention to design and develop a synthetic multi-level lamellar structure, e.g., scaffold, to mimic the prominent motif of lamellar plywood organization found in natural bone, in order to derive the benefits, e.g., mechanical and regenerative properties, exhibited by natural bone. In general, the lamellar structure includes multiple lamellae and each lamella includes stacked layers. The geometry varies and is also not limiting. The description provided herein is predominantly directed to circular, spiral and concentric lamellar structures for ease of description. However, it is understood that the invention is not limited to these specific shapes. In certain embodiments, circular layers are stacked (e.g., one on top of the other) to form each lamella. Multiple lamellae are then arranged to form concentric, nested layers. The stacked circular layers may be rotated or displaced at an angle. Additionally, each of the concentric, nested layers may be rotated relative to the others. That is, a rotation or a change in angularity may be exhibited across each of the lamella and/or between the multiple lamellae. The rotation or change in angularity is between 0 and 90 degrees. In certain embodiments, a spiral is formed wherein the pitch of the spiral is the height of one complete helix/spiral turn, measured parallel to the axis of the helix/spiral. Further, the rotation or change in angularity is in one or more of the x-, y- and z-directions.

Structural imaging analysis, e.g., micro-diffraction as well as X-ray micro-computed tomography image analyses, of the natural bone tissue is performed in order to ascertain its lamellar organization and architecture. Data obtained from the structural imaging analysis of the naturally occurring bone tissue is used to specify the design parameters of the biomimetic scaffold, and to determine angular displacement of lamella/lamellae within the rotated plywood lamellar structure. The data is used to achieve a synthetic scaffold having an overall orientation or trend mimicking that of the natural bone tissue. The scaffold design is made using micro-diffraction image analysis from quantitative data of natural bone tissue micro-diffraction, in the organization of concentric mineral-embedded fibrous layers splayed at periodic angular displacements from the surrounding fibrous layers. Through the use of micro-diffraction image analysis, quantitative structural elucidation data is extracted from various types of bone tissue with variations in parameters indicating possible mechanical significance, thus, representing a new level of biomimetic structural design. Information regarding the structure and construction of natural bone is obtained using a wide variety of tools and methods known in the art. In addition to micro-diffraction image analysis, other imaging modalities may be used to extract this information from natural tissue. For example, micro-diffraction image analysis, polarized light microscopy, SEM surface tomography, X-ray diffraction, X-ray diffraction tomography and X-ray micro computed tomography and the like, may also be used to gather information regarding structural construction of the natural material to be modeled in the biomimetic design.

The biomimetic structural motif includes sequential (e.g., consecutive), multiple layers of varying geometry, e.g., lamellae, arranged and oriented according to specific, non-regular patterns or trends. For example, in certain non-limiting embodiments, the biomimetic structural motif includes concentric layers. However, as mentioned, the invention is not limited to concentric layers, e.g., a cylindrical shape. For example, the biomimetic structural motif may include planar layers. Without being bound by any particular theory, it is believed that the arrangement and orientation, e.g., angularity, contributes to the improved properties demonstrated by the engineered scaffold following the motifs above through physical and mechanical characterization, and uniaxial compressive testing. Customizable shapes and configurations, and applications using this plywood structural motif as a foundation is achieved using a variety of the conventional additive manufacturing techniques. The scaffolds fabricated in accordance with the invention exhibit one or more of the following properties: increased elastic modulus, decreased strain at failure and approximately two-fold greater ultimate compressive strength, as compared to conventional plywood scaffold designs having similar bulk volume, surface area and fabricated density using the sample material composition.

In addition, the scaffolds of the novel biomimetic design also demonstrate one or more of the following characteristics: increased homogeneity of deformation between elastic and plastic regimes, micro-fracture crack deflection and negligible plastic deformation of the structure prior to radially symmetric failure, as compared to conventional plywood scaffolds. These conventional plywood scaffolds have been found to demonstrate asymmetric plastic buckling resulting in a significantly contorted macrostructure prior to failure.

In accordance with the invention, multi-level, three-dimensional structures are created by forming a plurality of aligned, parallel layers. The layers are composed of or constructed from a wide variety of resorbable and non-resorbable materials that are known for use in forming bone tissue scaffolds. Biomaterials normally selected for the construction of implant devices, e.g., scaffolds, are typically chosen based on their ability to withstand cyclic load-bearing and compatibility with the physiological environment of a human body. Implant devices are traditionally constructed from biodegradable and/or non-biodegradable metal or polymer or ceramic, or alloys, composites and blends thereof in the form of bioresorbable or non-resorbable permanent implants or scaffolds. These materials of construction exhibit good biomechanical properties. Metallic biomaterials, in particular, have appropriate properties such as high strength, ductility, fracture toughness, hardness, corrosion resistance, formability, and biocompatibility to make them attractive for load bearing applications. Non-limiting examples of suitable metals for construction of the implant device include iron, iron alloys, titanium, titanium alloys, cobalt-chromium alloys, biodegradable magnesium, biodegradable magnesium alloys, and mixtures and blends thereof. Polymers, such as polyhydroxy acids, polylactic acid (PLA), polyglycolic acid (PGA), polycaprolactone (PCL) and the like, are known as conventional biomaterials, however, in some instances the strength and ductility exhibited by polymers is not as attractive as that demonstrated by metallic biomaterials. Non-limiting examples of suitable ceramics for construction of the implant device include calcium phosphate, hydroxyapatite, tri-calcium phosphate, tetra-calcium phosphate, calcium phosphate cements, magnesium phosphate cements, and combinations thereof. Certain embodiments include a combination of calcium phosphate cement(s) and magnesium phosphate cement(s).

There is an inherent interest and focus to design and develop biodegradable construction materials for implant devices. There is typically a period of time after which an implant device is no longer needed, e.g., after bone or tissue healing is complete. The devices are left in situ or, alternatively, they are removed. Each of these alternatives has disadvantages or problems associated therewith. For example, leaving the device in situ increases the probability and risk of infection and rejection, consequently, removal of the device requires a second surgery which also causes a risk of infection, complications leading to additional fracture, pain and discomfort to the patient, as well as it being an additional expense. To overcome these disadvantages or problems, there has been developed a number of bioresorbable polymeric devices that are effective in degrading over a period of time, e.g., by dissolving in the physiological environment. Thus, the device does not remain in-situ and there is no need to surgically remove the device because when the device is no longer needed, the polymeric biomaterial degrades or dissolves within the patient body.

However, there are also disadvantages associated with the bioresorbable polymer devices. For instance, it has been found that the bioresorbable polymeric materials, which are used for the construction of biodegradable medical implant devices, can lack mechanical strength as compared to that exhibited by metal implants and have a limited set of applications. As a result, there is an interest in the art to identify materials that degrade over time, while also demonstrating sufficient mechanical strength prior to degradation.

Pure magnesium and magnesium alloys are attractive as biomaterials for the construction of bioresorbable devices because they have mechanical properties compatible to bone and resorb over a period of time. For example, magnesium is very lightweight, has a density similar to cortical bone, has an elastic modulus also close to natural bone, is essential to human metabolism, as well as is a cofactor for many enzymes, and stabilizes the structures of DNA and RNA.

The biomaterials suitable for use in constructing the multi-level lamellar biomimetic structure, e.g., scaffold, of the invention include metals, metal alloys, polymers, ceramics and blends thereof. The biomaterials can be biodegradable, non-biodegradable, bioresorbable, non-bioresorbable, bioabsorbable, non-bioabsorbable, biocompatible, bio-inert, bioactive and combinations thereof. The scaffold is formed by an additive manufacturing technique, such that each layer is formed, stacked and aligned parallel to another layer. For example, a first base layer having an upper surface is formed, a second additive layer is formed and aligned parallel with the upper surface of the first base layer (e.g., the second additive layer having a lower surface parallel with the upper surface of the first base layer), and a third additive layer is formed and aligned parallel with an upper surface of the second base layer (e.g., the third additive layer having a lower surface parallel with the upper surface of the second base layer). This additive process and arrangement continues for subsequent layers until a desired number of layers are formed to construct the scaffold. These layers represent any sequence of multiple layers of varying geometry, such as, but not limited to, concentric layers of circular geometry (e.g., rings). In certain embodiments, the scaffold includes multiple sheets/lamellae of stacked, parallel aligned rings, wherein the multiple sheets/lamellae are formed in a nested configuration, such that the inner sheet/lamella has layered rings of a smaller diameter as compared to the diameter of the layered rings in the outer sheet/lamella. In accordance with the invention, each of the first, second and third rings is rotated or angularly displaced from the longitudinal axis at controlled spacing, and the distance between the rings also may be spatially controlled. Furthermore, the nested layers formed from the sheets of layered rings, are rotated or angularly displaced from one another at controlled spacing, and the distance between the sheets also may be spatially controlled.

There are various additive manufacturing techniques, and associated apparatus, that are known in the art for fabricating the synthetic scaffolds. Non-limiting examples of suitable additive techniques and apparatus include, but are not limited to, solid free-form and layered manufacturing processes, such as, 3-D printing processes, e.g., binder-jet-3-DP, fused deposition modeling (FDM),and laser as well as electron beam processes. Generally, conventional binder-jet-3-DP processes include providing as input to a system, e.g., computer, the specific structure that mimics natural bone tissue. The flexibility of the software used in the system allows for various changes in angularity and displacement of the layers. Each layer is fed to the 3-D printer for printing in accordance with the additive technique. The layers, for example, can be changed in the x-y direction or the y-z direction or the x-z direction, as well as the various angles between the x-y direction or the y-z direction or the x-z direction allowing for a complete 6-axis rotation capability depending on the printing technique.

As aforementioned, the scaffolds fabricated in accordance with the invention are designed to mimic the mechanical properties and characteristics associated with the natural bone tissue. As described, it has been found that natural bone tissue has a lamellar plywood organization including subsequent layers, e.g., lamellae, of parallel mineral-embedded microfibers rotated to create an overall spiral twist, which then organize into cylindrical units referred to as osteons. Without intending to be bound by any particular theory, it is believed that the rotation or angular displacement, e.g., within a plane, of one layer relative to another layer results in the ability to form scaffolds that mimic the properties and characteristics exhibited by natural bone tissue. Further, as described, the layered organization and arrangement of a particular type of natural bone tissue is ascertained by a structural analysis, and the data obtained from the analysis is used to determine the organization or angular orientation of the layers in the composite structure. More particularly, the data indicates how each of the layers in the composite structure are to be rotated or displaced at an angle, e.g., rotational angle(s), relative to another layer, in order for the layers in the scaffold to mimic the layer organization and orientation of the natural bone tissue. This information and data serves as the input into a printing process, e.g., a 3-D printing process including a computer and associated software, for producing the additively manufactured lamellar structure.

The rotational angle for each of the layers, e.g., lamella, varies and is dependent on the lamella orientation of the specific natural bone tissue that the synthetic scaffold is to mimic. In general, each rotated or displaced layer has an angular rotation (e.g., degrees) measured off the longitudinal axis, however, the number of degrees will be determined based on the lamella orientation of the natural bone tissue. In certain embodiments, each of the layers will be rotated or displaced to form an overall orientation or a trend based on, e.g., commensurate with, the overall orientation, e.g., twist or angularity, of the natural bone tissue. In certain embodiments, the angular rotation of the layers is from 0 degrees to 90 degrees.

The scaffold fabricated in accordance with the invention includes various shapes, such as, but not limited to, a cylinder. Each of the various shapes can include multiple layers. For example, a cylinder includes multiple layers of circular geometry, e.g., rings. As described herein, the cylinder includes multiple cylindrical layers. The layers of rings are nested concentrically such that there is formed an inner cylindrical layer, an outer cylindrical layer and one or more, a plurality of, parallel layers positioned between the inner and outer layers, e.g., nested concentric lamellae. Further, in accordance with the invention, one or more of the cylindrical layers are each rotated at a controlled angle relative to another cylindrical layer. The overall architecture or trend, is a spiral twist formed by the angled cylindrical layers (e.g., to mimic the overall spiral twist architecture of natural bone tissue). In certain other embodiments, the layers of the scaffold are in the form of thin sheets. Each sheet are oriented at an angle, e.g., in the plane, relative to another sheet.

In accordance with the invention, for example, a stack of circular layers, e.g., rings, within each lamella, e.g., a sheet, is rotated angularly. The rotation is from 0 degrees to 90 degrees off of the longitudinal axis of the sheet. In addition, there is a plurality of lamellae, e.g., nested sheet, and each sheet is angularly rotated in relation to one or more of the other sheets.

FIG. 1(a) shows a computer-aided design (CAD) 3D image of a cylinder-shaped composite, which includes a rotated plywood motif for strut lamellae, e.g., spiral twist. The outer two layers are transversely sectioned to show the orientation of the inner layer. The composite exhibits three nested concentric lamellae of alternating mesh pattern struts with circular cross section. For this "alternating" scaffold, there are three lamellae having angular rotations of 68, 25, and 80 degrees off the longitudinal axis, from the outermost lamellae to the innermost lamellae, respectively. Thus, the circular layers (e.g., rings) in each of the three lamellae are rotated or exhibit a change in angularity across each of the lamellae. Additionally, in accordance with the invention, each of the three lamellae are rotated or exhibit a change in angularity between the lamellae. Thus, there is rotation or change in the angularity across each of the lamellae or layer (which allows for control of the orientation and deposition of the "building blocks", e.g., rings), and between the lamellae or layers. It is anticipated and understood that a composite in accordance with the invention may be in the shape of a planar rotated/twisted plywood motif, in addition to the concentric rotated/twisted plywood motif shown in FIG. 1(a).

Figure 1B:
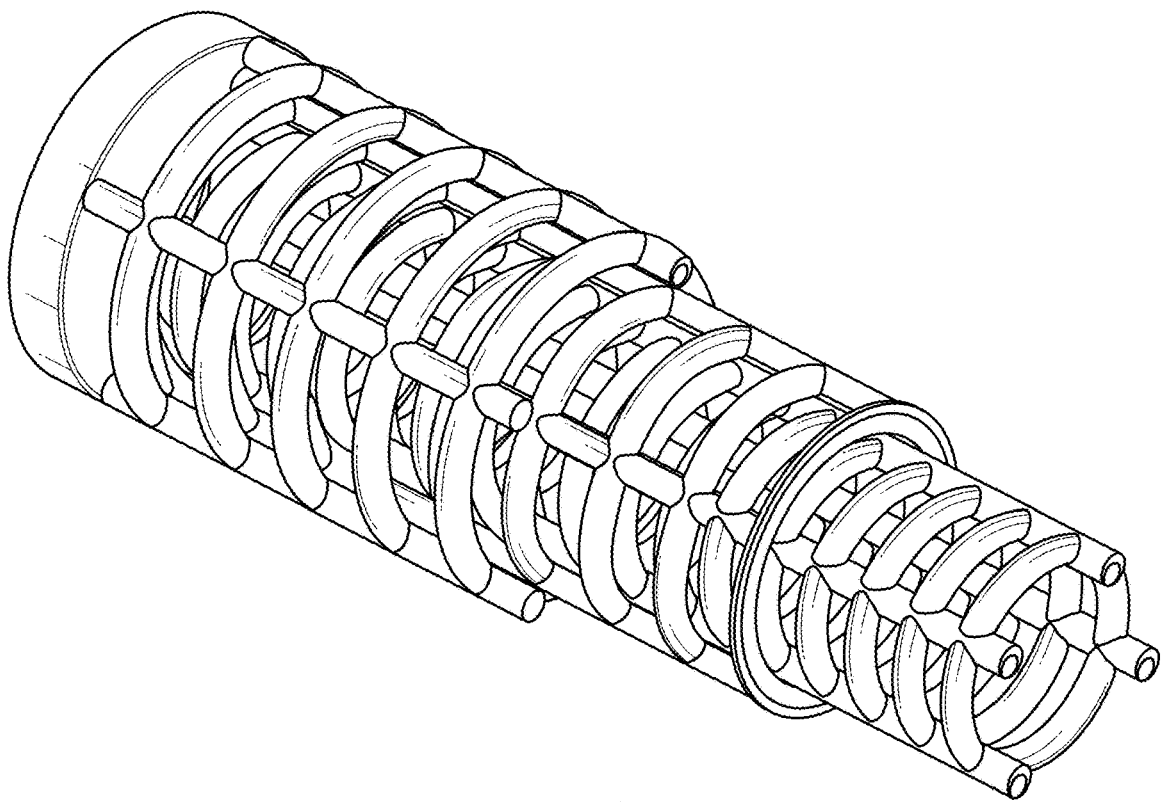

FIG. 1(b) shows a CAD 3D image of a cylinder-shaped composite, wherein the strut lamella features have the same strut dimensions and, transverse and longitudinal inter-strut distance, e.g., an orthogonal design, as compared to the alternating design shown in FIG. 1(a). For this "orthogonal" scaffold design, three nested concentric orthogonal lamellae, having the same mesh pattern struts, are oriented along a cylindrical longitudinal axis and transverse planes. Longitudinal and transverse struts are aligned in the radial outward direction.

It is contemplated and understood that in addition to the angular rotation or displacement of the layers, the strut dimensions and design also vary. For example, as shown in FIG. 1(a), the ring orientation for one layer differs from the ring orientation of another layer or other layers. Further, the strut, e.g., hollow space between the rings, for one layer differs from the strut orientation of another or other layers. Furthermore, the distance between the parallel sheets/lamellae varies.

EXAMPLES

The merits of a biomimetic scaffold design in accordance with the invention were compared with conventional mesh scaffold designs. Scaffolds were characterized under uniaxial compression testing, followed by scanning electron microscopy and micro-computer tomography analyses. Observation and connection of failure defects at the microstructural level to overall bulk scaffold mode of failure, led to the conclusions that utilizing a biomimetic lamellar plywood design improved scaffold performance similarly to native tissue by, not only, improving mechanical performance, but also mode of failure in more complex, hierarchical behaviors such as the mode of crushing and fracture propagation.

Mechanical performance of similar fiber-reinforced composite materials was previously evaluated through analysis of stress-strain performance, crushing modes, and their associated crushing mechanisms which contribute to the overall structural failure under compressive loading. Although ply orientation was previously implicated in composite energy absorption, it was an objective in the following example to relate this previous insight to bone tissue engineering through investigation of mechanical performance of a complex biomimetic structure. A secondary aim in the following example was to investigate the causes of possible underlying structure-associated trends of failure mechanisms primarily by applying imaging analyses employing scanning electron microscopy (SEM), as well as micro-computed tomography ($\mu$CT) analysis exploiting quantitative and qualitative modes to generate predictive concepts related to bone regeneration.

Materials & Methods

Scaffold Design

Two scaffold designs were generated using Autodesk Inventor software featuring lamellar strut orientation variations on a hollow cylinder design. Height and diameter of the samples were 36.0 and 12.0 mm respectively, with an inner diameter of 6.0 mm. Both designs exhibited three nested concentric lamellae of orthogonal mesh pattern struts with circular cross section of diameter 1.0 mm for a total layer thickness of 3.0 mm. Vertical and horizontal distance between struts for both scaffold designs are exhibited in Table 1 for each lamellae.

TABLE 1

Measured distances between struts controlled in both alternating and orthogonal scaffold designs for concentric scaffold lamellae.

| Layer | Longitudinal Distance (mm) | Transverse Distance (mm) |
| --- | --- | --- |
| Innermost | 4.07 | 0.91 |
| Middle | 2 | 5.41 |
| Outermost | 2.24 | 7 |

For the "orthogonal" scaffold design, orthogonal lamellae were oriented along the cylindrical longitudinal axis and transverse planes. Longitudinal and transverse struts were aligned in the radial outward direction to mimic the straight porous channels implemented in previous SFF scaffold designs. For the "alternating" scaffold featuring the biomimetic rotated plywood structural motif, quantitative lamellar angular rotation data was extracted from previous structural elucidation of secondary human bone osteons carried out using X-ray microdiffraction. Due to constraints of the fabrication process, a representative section of the total quantitative microdiffraction structural data was used in scaffold design to accommodate for simplification of 3 lamellae in a hollow cylindrical model for angular rotations of 68, 25, and 80 degrees off the longitudinal axis, from the outermost lamellae inward. The alternating scaffold design is shown in FIG. 1(a) and the orthogonal scaffold design is shown in FIG. 1(b).

Figure 2A:
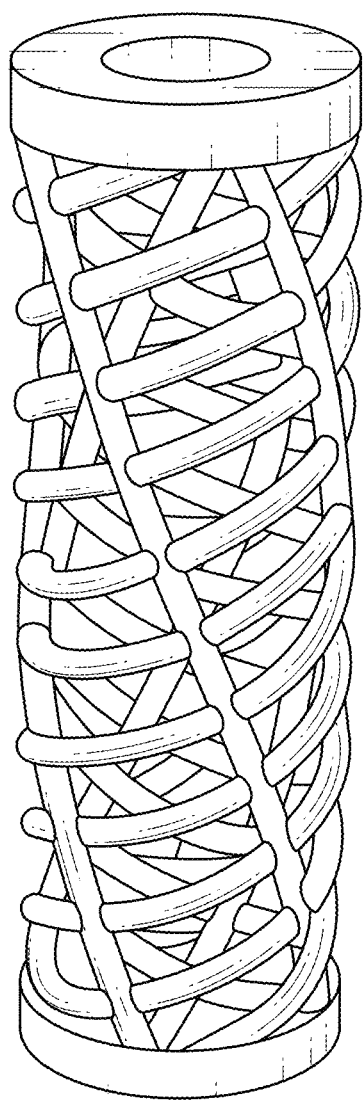
FIGS. 2(a) and 2(b) are images of the scaffolds in FIGS. 1(a) and 1(b), respectively, after fabrication and post-processing.
Figure 2B:
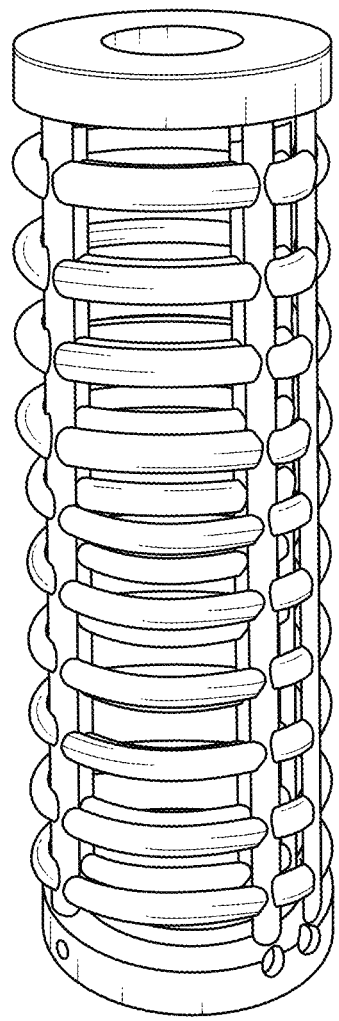

Based on the CAD data, scaffolds (n=13 for each design) were fabricated by means of a binder jet 3D printing process ((The ExOne Company, LLC, North Huntingdon, Pa.) from iron (Fe) powder with average particle size of ~45 μm (99%, Höganäs AB, Höganäs, Sweden). Printed green constructs were cured at 185° C. for one hour, then de-powdered using pressurized air and sintered at 1100° C. for three hours. A fabricated alternating design scaffold is shown in FIG. 2(a) and a fabricated orthogonal design scaffold is shown in FIG. 2(b).

Scaffold Physical Properties

Porosity values for scaffolds were calculated according to both CAD engineered porosity and fabrication introduced porosity (in binder-jet 3D printing, curing, and sintering processes). Engineered CAD porosity was calculated according to the following equation:

$$\frac{(V_{cyl} - V_{sc})}{V_{cyl}} \times 100\%$$

where $V_{sc}$ is the total volume of the CAD scaffold design and $V_{cyl}$ is the overall volume of the theoretical hollow cylinder enclosed by the outer and inner peripheries.

Unsintered and sintered porosities represented deviation in scaffold material density compared against a theoretical density of pure iron and did not include engineered CAD porosity of overall scaffold designs. These were calculated according to the following equation:

$$\left(1 - \frac{\rho_{sc}}{\rho_{Fe}}\right) \times 100\%$$

where $\rho_{Fe}$ is the density of non-porous iron (7.874 g/cm3) and $\rho_{sc}$ is the density of the manufactured scaffolds (before or after sintering), calculated using the weight and volume of the scaffolds (n=3 for orthogonal, n=2 for alternating, unpaired).

Mechanical Testing

Compressive testing was conducted in accordance with ASTM-E9. Uniaxial compressive testing was performed with sintered scaffolds at room temperature with an Instron 5566 mechanical testing system (Instron, Norwood, Mass.) using a cross-head speed of 3 mm/min and a 5 kN load cell. Ultimate compressive strength, Young's modulus, and strain (percent elongation) at failure were determined from stress-strain curves generated from each specimen. Young's modulus was obtained as the slope of linear regression over the elastic performance region of each stress-strain curve. Ultimate compressive strength and strain at failure were determined as the maximum compressive stress and corresponding strain. Average, standard deviations, and one-way independent ANOVA results for both scaffold designs (n=8 for each design) are reported.

Scanning Electron Microscopy

Scanning electron microscopy (SEM) images were also taken of sintered scaffolds before and after uniaxial compressive testing using a Philips-XL30 FEG (Philips, Amsterdam, the Netherlands) at 10.0 kV at various magnifications for surface fracture analysis.

MicroCT

Scaffold specimens (n=3 for each design) were scanned with a VivaCT40 (Scanco Medical AG, Bruttisellen, Switzerland) and 30 um voxel size (70 kV, 110 uA). For analysis, scanned scaffold volumes were digitally reoriented, filtered from background signal, and converted to .stl format for standardized quantitative analysis using Mimics Medical 17.0 (Materialise NV, Leuven, Belgium). For directionality analysis of the different modes of failure between scaffold designs, outward deformation measurements in radial step size of 30 degrees were taken at transverse slices of 5 mm step size for each scanned specimen, and plotted as a deformation profile illustrating significant variations in radial direction of deformation.

TABLE 2

Porosities calculated from CAD and for fabricated specimens given as mean ± standard deviation, total surface areas, and average cross section areas calculated from CAD.

| Design | Porosity | | | Surface area | Volume | Average CS area |
|---|---|---|---|---|---|---|
| | CAD | Unsintered | Sintered | | | |
| Orthogonal | 53% | 15.5 ± 2.5% | 8.1 ± 3.3% | 46.71 cm$^2$ | 1.436 cm$^3$ | 0.4047 cm$^2$ |
| Alternating | 54% | 15.2 ± 3.1% | 14.3 ± 2.3% | 45.62 cm$^2$ | 1.407 cm$^3$ | 0.2087 cm$^2$ |

Results

Scaffold Porosity

Calculated porosities, total surface area, and average cross sectional surface area for CAD scaffold designs and fabricated samples are listed in Table 2. Both scaffold designs exhibited an engineered porosity of approximately 53-54%, while additional porosity in the 3-DP fabrication process was introduced at approximately 15% for all unsintered specimens. After sintering, material porosity decreased for both scaffold designs to approximately 8% for orthogonal specimens (n=6) and 14% for alternating specimens (n=4). Variations in porosity introduced through the fabrication process was less than 5%. Total surface area for both scaffold designs was approximately 46 cm$^2$, while scaffold volumes were calculated to be 1.436 cm$^3$ for the orthogonal design and 1.407 cm$^3$ for the alternating design. Greater variation was seen in the average calculated scaffold cross section area, with 0.4047 cm$^2$ for the orthogonal design and 0.2087 cm$^2$ for the alternating design.

TABLE 3

Scaffold specimen mechanical properties, given as mean ± standard deviation.

| Scaffold design | Elastic modulus (GPa) | Ultimate compressive strength (MPa) | Ultimate compressive strain (%) |
|---|---|---|---|
| Orthogonal | 0.196 ± 0.158 | 6.309 ± 2.308 | 9 ± 2.243 |
| Alternating | 1.320 ± 0.369 | 16.546 ± 2.292 | 4.867 ± 1.017 |

N = 8 for each scaffold design.

Mechanical Behavior

Figure 3:
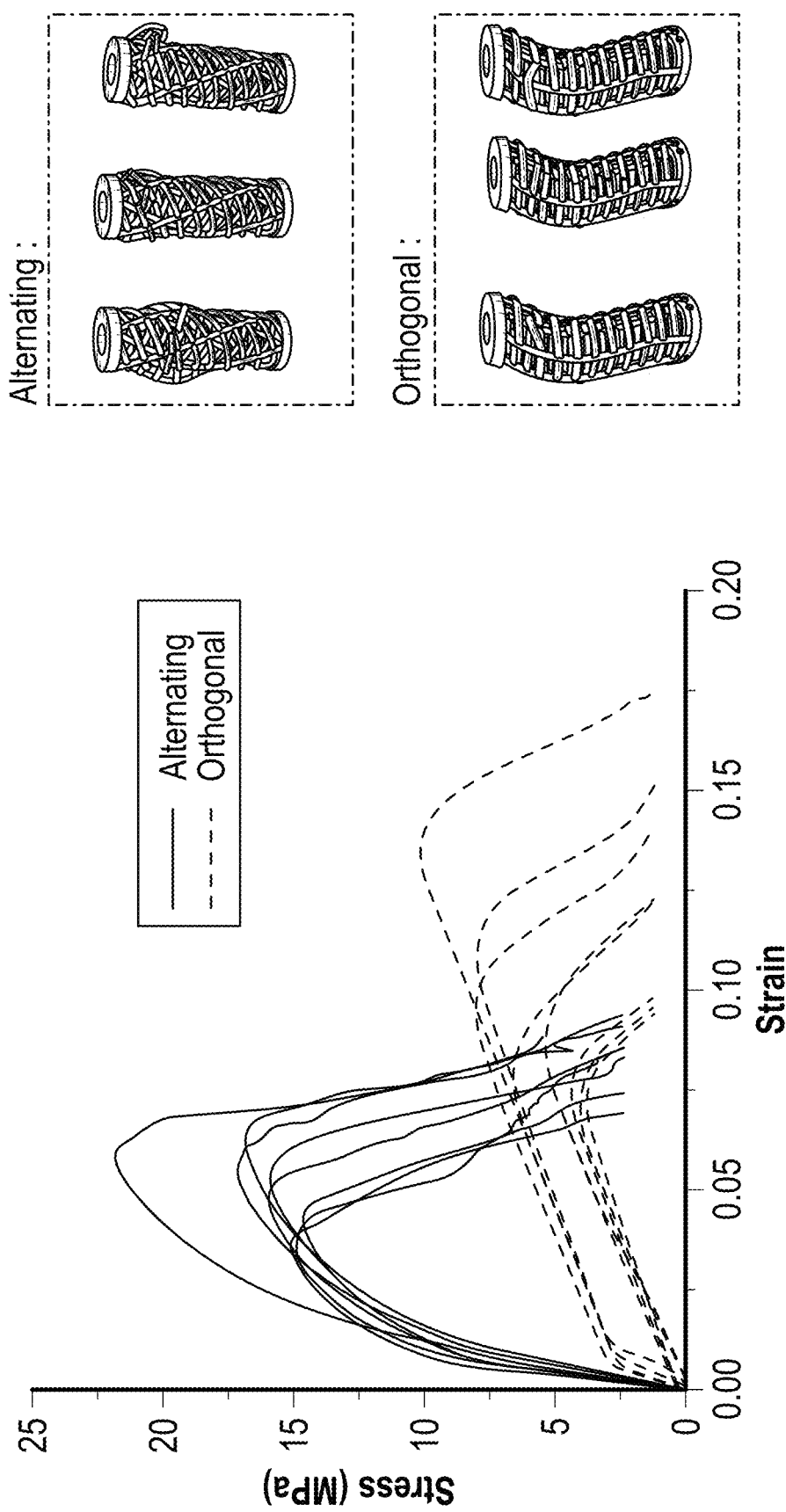
FIGS. 3 and 4 are plots of engineering stress-strain relationships for alternating and orthogonal scaffold designs in accordance with the invention, and FIG. 3 includes photographs showing the results of mechanical failure of the scaffolds.

Stress-strain relationships plotted in FIG. 3 were calculated using values for average cross sectional area for respective scaffold designs. The stress reflects the force acting upon the overall scaffold structure and does not represent the stress within individual struts.

Significant variation is illustrated in the stress-strain plots for all of the compressed samples between the two scaffold designs (n=8 each). Orthogonal and alternating specimens varied in slope of stress against strain immediately following start of compression in the elastic performance region (shown in FIG. 4). Orthogonal design specimens demonstrate a distinct transition from elastic to plastic performance in change of slope with positive linear trends for both regimes. Alternating design specimens demonstrate no discrete change in slope from start of compression to peak load at failure. Performance is instead characterized by a gradual, curved trend. Scaffold performance after failure for alternating design specimens was characterized by interruptions in decreasing trend after peak load, while orthogonal designs featured smooth decreases in the stress-strain relationships.

Figure 4:
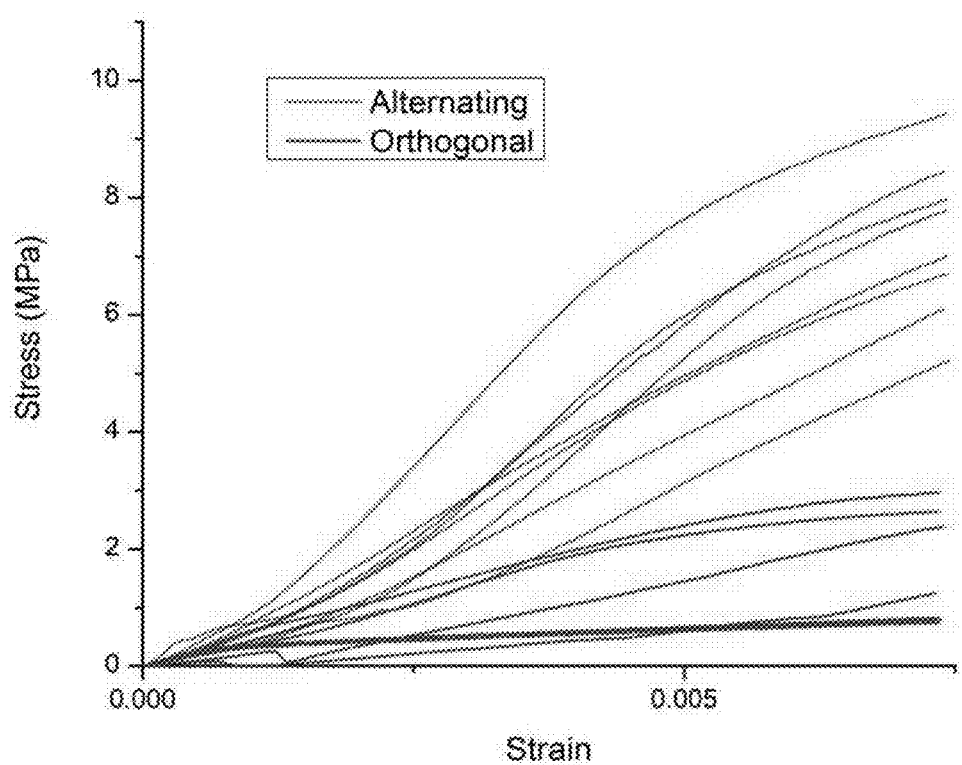
Figure 5A:
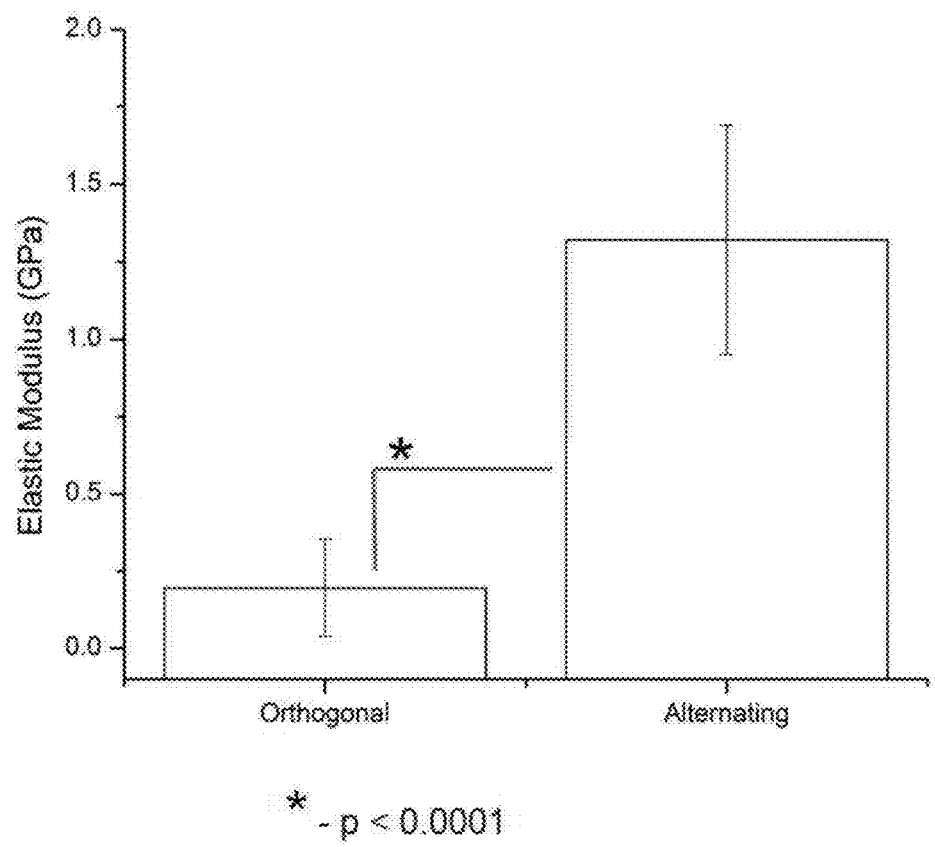
FIGS. 5(a), 5(b) and 5(c) are plots of elastic moduli, ultimate compressive strength and strain at failure, respectively, for alternating and orthogonal scaffold designs.
Figure 5B:
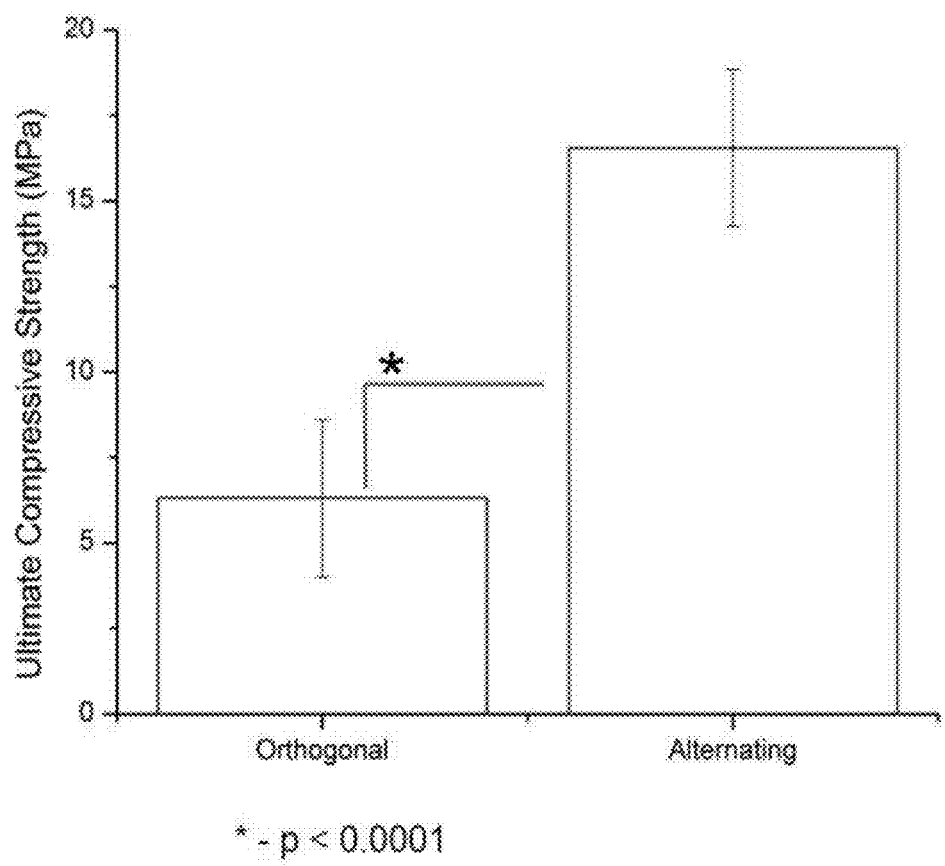
Figure 5C:
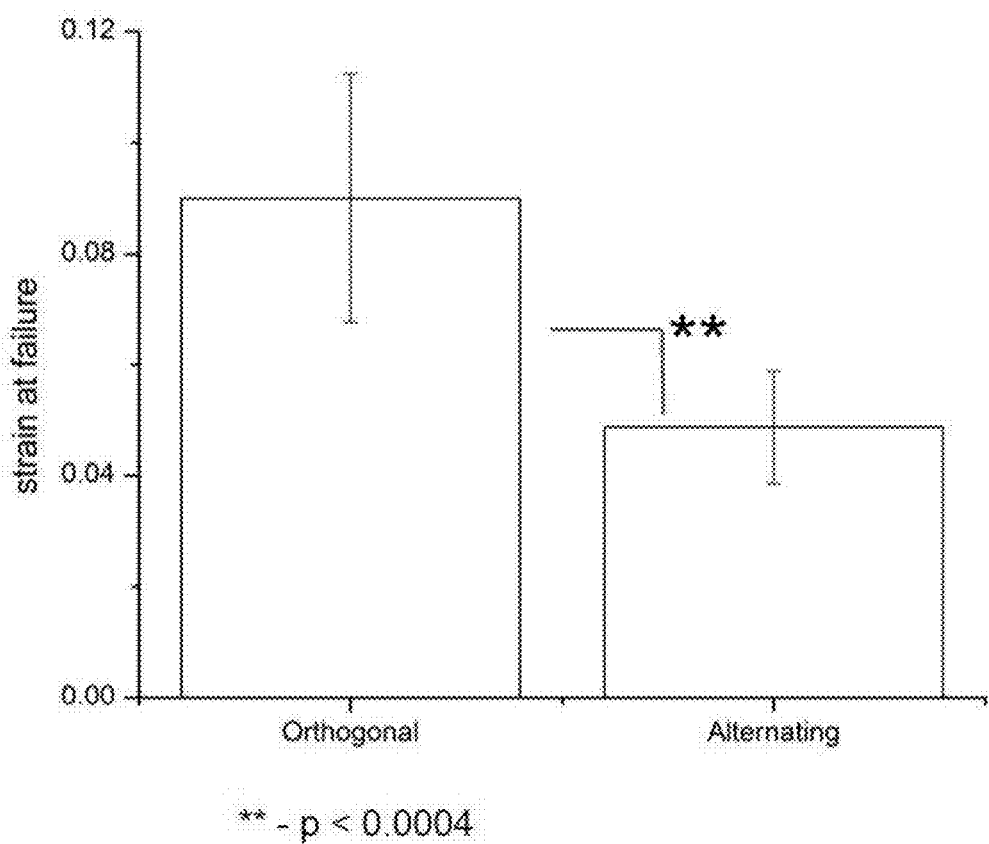

Scaffold mechanical properties shown in Table 3 were derived from the stress-strain relationships plotted in FIG. 3. The elastic modulus was calculated using linear regression of the region of elastic response (FIG. 4). Ultimate compressive strength was defined as the peak stress measured before scaffold failure. Ultimate compressive strain was defined as the strain corresponding to the ultimate compressive strength. Values in Table 3 are plotted in FIGS. 5(a), (b), and (c) in the form of means (n=8 for each scaffold design) with error bars signifying standard deviation. Brackets between bars indicate significance by one-way independent ANOVA (MATLAB). Alternating scaffolds featured higher elastic modulus ($p<0.001$), higher ultimate compressive strength ($p<0.001$), and lower strain at failure ($p<0.004$).

SEM Analysis

The morphology of both 3-DP scaffold types are shown in FIG. 2 before uniaxial compressive testing. No significant variations in particle size, extent of sintered porosity, or microstructure were observed. Qualitative surface analysis shows a porous topography confirming previous applications of 3-DP scaffold applications. Although printed scaffolds were not surface finished, no significant oxide layer was observed.

Figure 6:
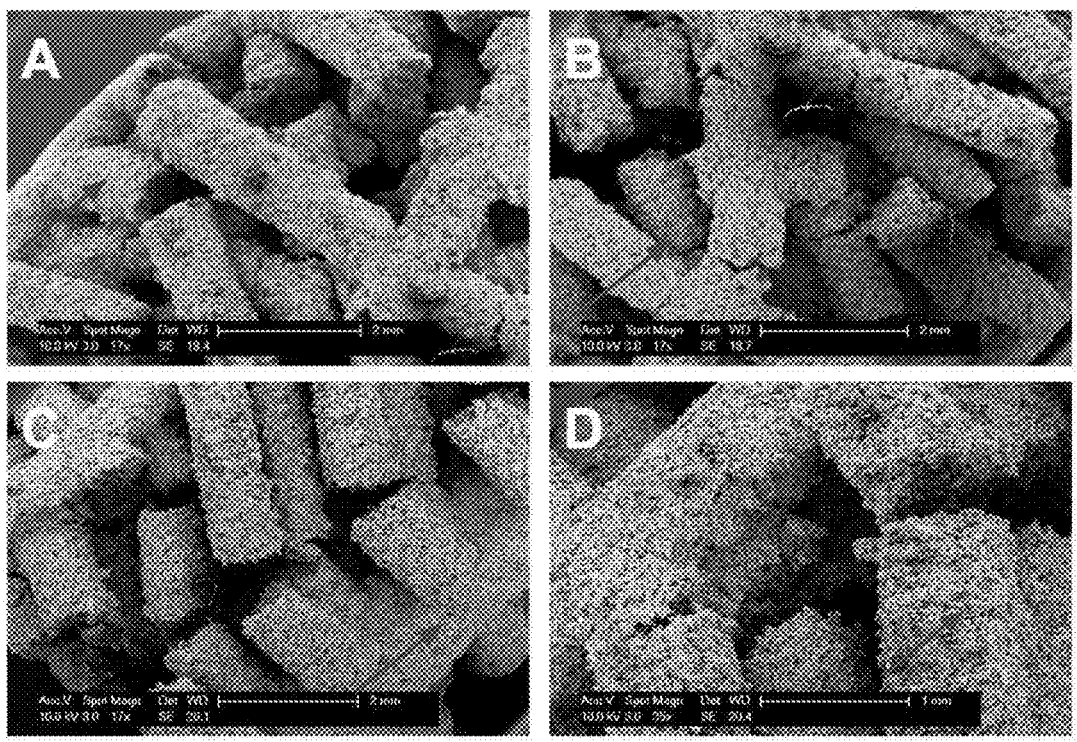
FIGS. 6 and 7 are images showing failure characterization for alternating and orthogonal scaffold designs through micro-fracture analysis.
Figure 7:
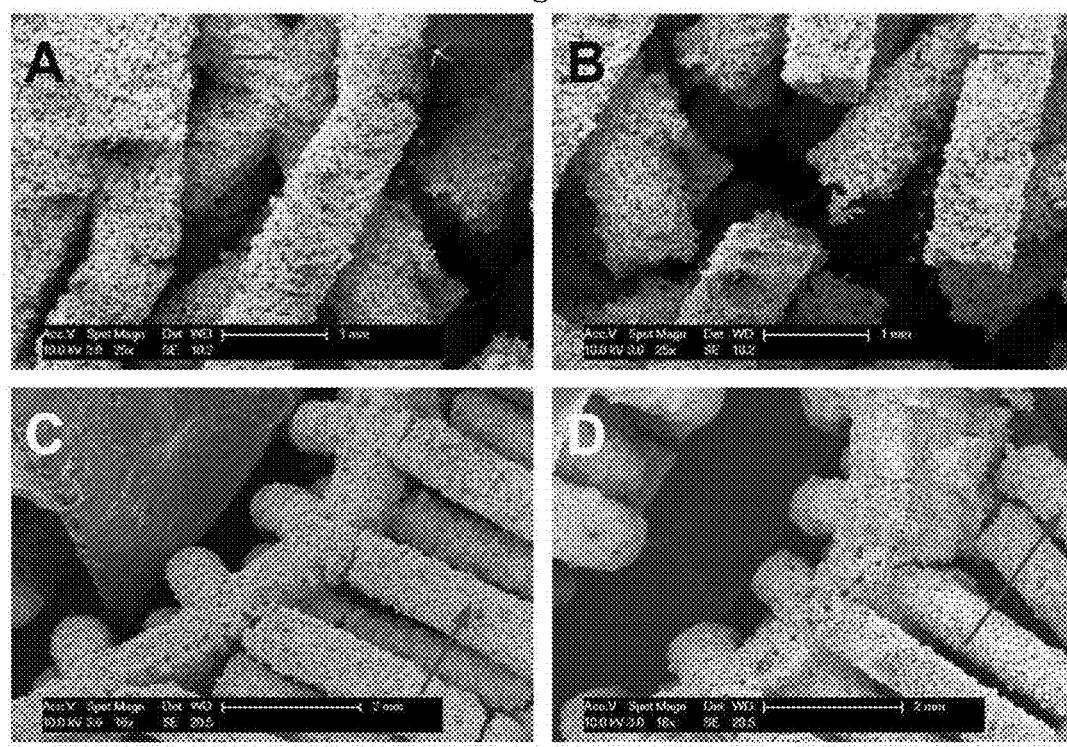

FIGS. 6 and 7 show failure characterization for both types of 3-DP scaffolds through microfracture analysis. FIGS. 6A and 6B illustrate typical fracture propagation through alternating design specimens. Both intralamellar and interlamellar fractures varied in orientation with respect to the longitudinal axis (indicated by the arrow), and depth on the transverse plane. Scaffold struts were also shown to fracture at different locations respective to intralamellar strut junctions. This mode of highly disorganized and deflected fracture propagation was consistent across the entire scaffold surface area in regions of failure for all alternating design specimens, in contrast against orthogonal design specimens, as represented in FIGS. 6C and 6D. Failure microfractures, while misaligned in alternating design specimens across a range of angular orientations, showed a high level of organization in both the longitudinal and transverse directions in orthogonal design specimens (longitudinal axis indicated by the arrow) and affecting multiple strut lamellae. It was seen that occurring at the same angular orientation and location with respect to the lamellar strut junctions, propagated fractures of greater continuous length and cross-sectional area were observed in the orthogonal design scaffolds.

Figure 8:
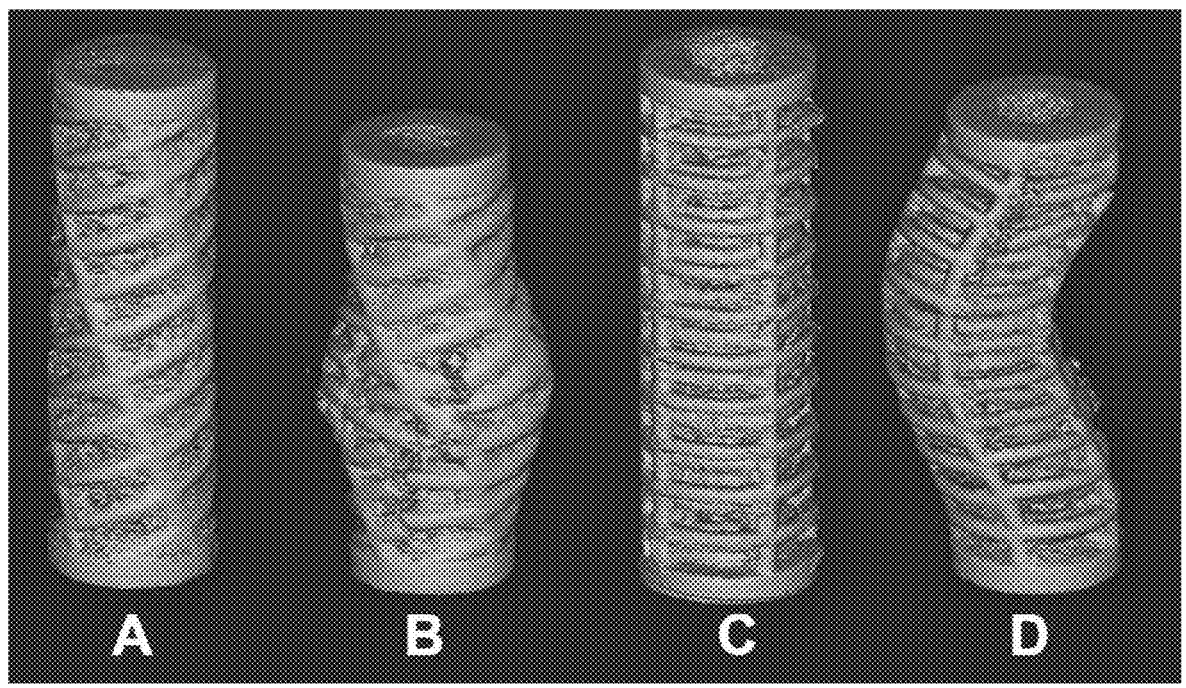
FIG. 8 is a micro-CT image for alternating and orthogonal scaffold designs before and after compression.
Figure 9:
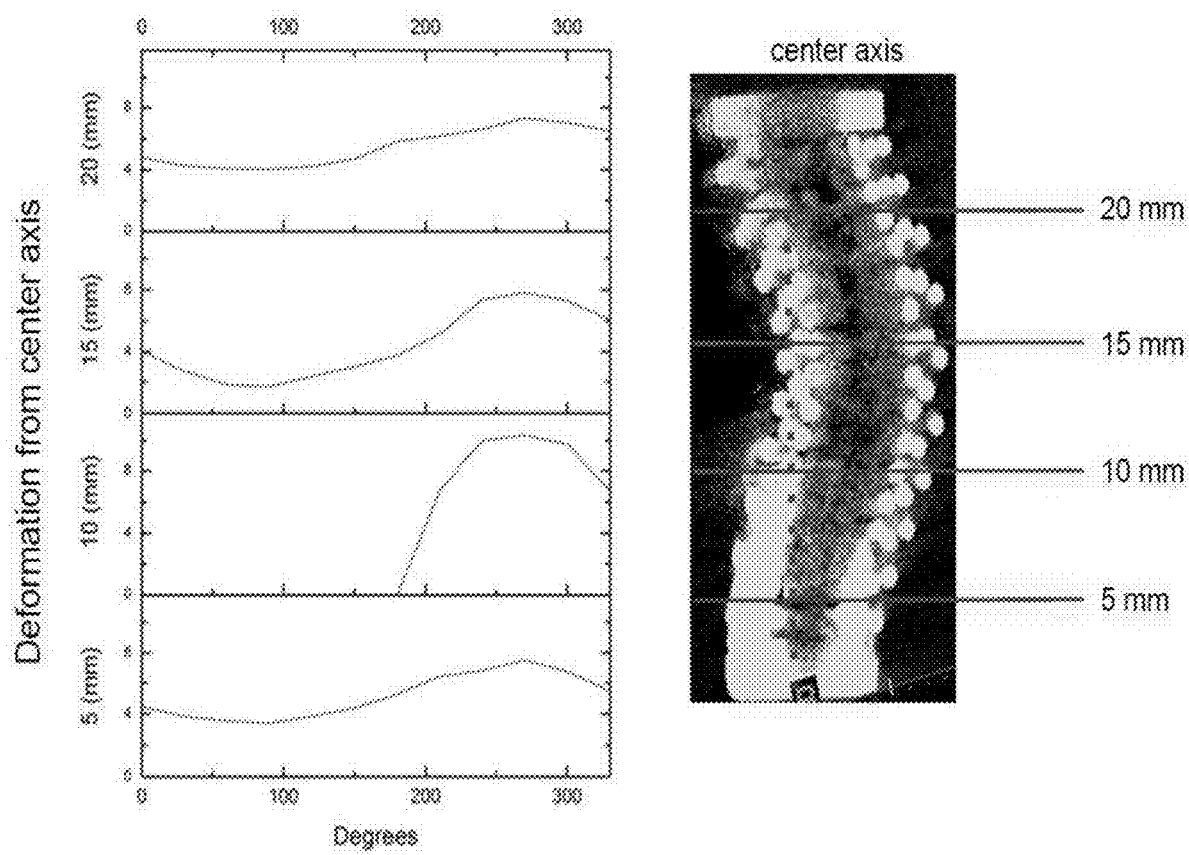
FIGS. 9 and 10 are plots and photos showing a deformation profile of orthogonal and alternating scaffold designs, respectively.

FIG. 7 shows distinctions in individual strut performance before failure between the two scaffold designs. Struts in alternating design specimens underwent minimal plastic deformation before brittle fracture as shown in FIGS. 7A and 7B. While microfracture initiation is apparent in FIG. 7A, the strut itself remained unbent, a trend reflected in fractured struts as in FIG. 7B, where fractured strut ends were also observed to have undergone little plastic deformation. This is contrasted in orthogonal design specimens as shown in FIG. 7C and 7D, where extensive asymmetrical plastic deformation can be observed. Plastic deformation occurred prior to strut fracture as illustrated in FIG. 7C in orthogonal design specimens, where fracture propagation has not yet fully occurred through the horizontally oriented struts (longitudinal axis indicated by the arrow), while FIG. 7D shows the aftermath of complete strut fracture after undergoing significant plastic deformation. Regions of greatest plastic deformation corresponded to asymmetrical buckling in scaffold overall structure, and were observed adjacent (nearest strut junction) to the large, continuous fractures noted in FIG. 6C.

uCT Analysis 3D renderings of representative scanned scaffolds are exhibited in FIG. 8 and show distinct trends of deformation behavior resulting from compressive loading. Orthogonal design specimens featured severe asymmetric buckling and plastic deformation of longitudinal struts before extensive continuous fracture propagation through transverse struts parallel to the scaffold longitudinal axis. Radial position of these multi-strut fractures commonly occurred orthogonally to direction of plastic buckling. This failure mode characteristic of orthogonal design scaffolds was reflected in the deformation profile in FIG. 9. Especially evident as transverse graphs progress toward the scaffold middle section, deformation distance followed a negative trend under approximately 150 degrees and an increasing trend over approximately 150 degrees. Deformation trend took on an increasingly sinusoidal appearance characteristic of circular linear translation. A buckling radial direction typical of orthogonal design specimens can be identified as the angular position of the peak maximum in the 10 mm deformation graph. Opposite to this direction, the specimen wall featured inward deformation following the pattern of outward deformation exemplifying plastic buckling behavior.

Figure 10:
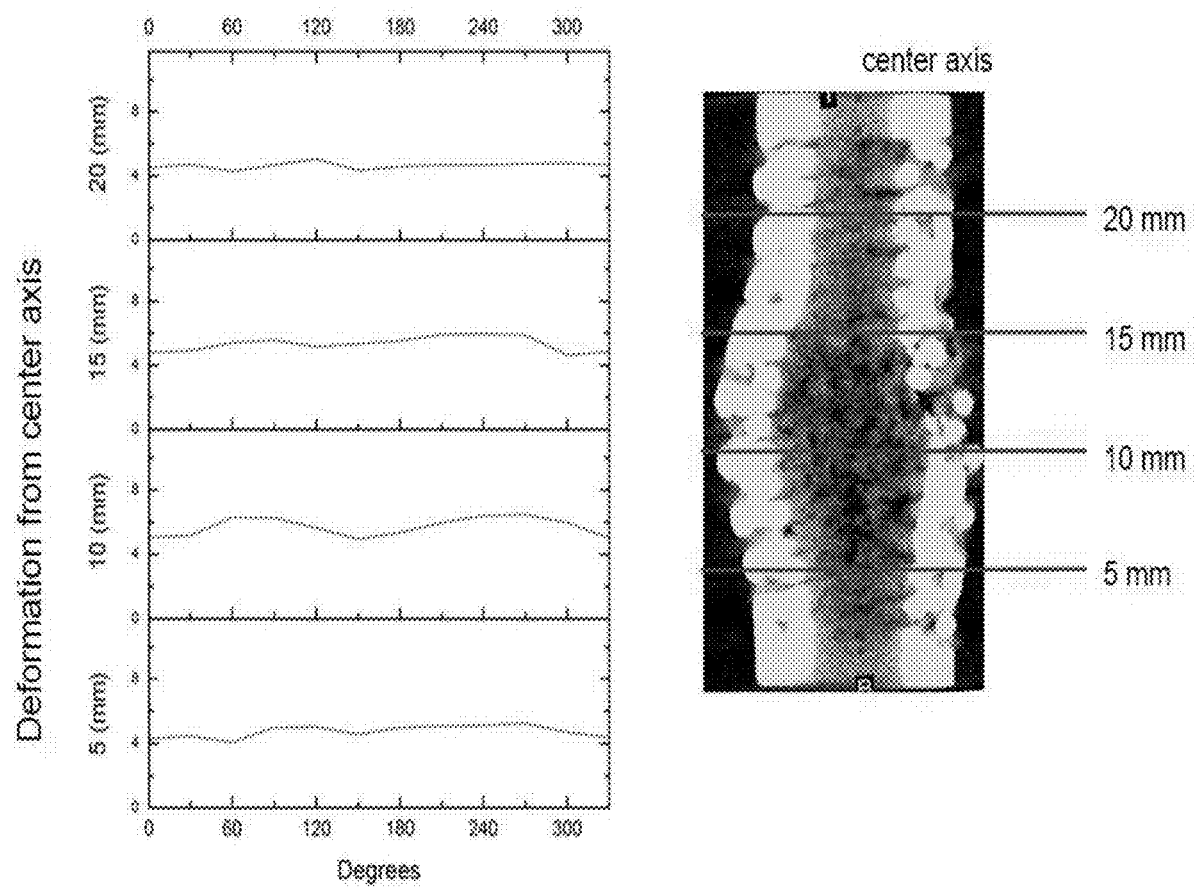

In contrast, deformation trends typical for alternating design specimens plotted on same axes scales show a significant decrease in variability for all the transverse sections as exhibited in FIG. 10. There remains a similar increasing trend in deformation distance as sections approach the region of failure. However, deformation distance did not depend on radial position, and no apparent maximum could be identified as in the deformation trends of orthogonal design scaffolds. This distinct mode of failure deformation was apparent in the 3D rendering in FIG. 8 as a general radial outward crumpling of the scaffold wall. Plastic deformation was much less severe compared to the orthogonal design scaffolds, with homogenous distribution of the smaller single-strut fractures over the entire surface of the failure region. No regions of inward deformation were identified for any of the alternating design specimens.

Discussion

In the examples, there was evaluated changes in 3-D fabricated scaffold mechanical performance arising solely from variation in structural geometry using the biomimetic lamellar rotated plywood structural motif An objective in applying the biomimetic approach to scaffolds for bone was to possibly replicate certain specialized behaviors of natural tissue in the scaffold performance while demonstrating significant changes in the scaffold mechanical properties. Another objective was to demonstrate that other distinctions in performance, such as mode of failure, fracture propagation, and extent of plastic deformation, may also arise from variation in structural organization and may be significant for future tissue engineering implant applications.

Fabrication of the complex scaffold designs with internal architectures was made possible through the use of SFF binder-jet printing techniques. Still another objective was to determine the specific mechanistic origins of variations in mechanical performance for these different architectures. Other methods of additive manufacturing, such as fused deposition modeling (FDM), laser or electron beam melting, have however, seen relative success in producing similar strengths against cast and wrought samples as well. Investigation of structural impact on performance, being independent to material composition or mode of fabrication, may be easily adapted to these other methods of additive manufacturing.

Statistical analyses performed on mechanical properties extracted from the stress-strain relationships for the orthogonal and alternating scaffold designs revealed significant variation in elastic modulus, ultimate compressive strength, and ultimate compressive strain, with alternating design specimens being higher in the first two and lower in the last. One possible contributing factor to these variations in performance is the significantly lower cross sectional area for the alternating scaffold design as exhibited in Table 2. This was likely the result of geometric lamellar orientation, as total scaffold volume, surface area, and engineered porosity were relatively similar between the two designs. These similarities support claims of structural orientation significance by controlling for other design differences between the two scaffold types (aside from sintered scaffold porosity). Because alternating scaffold lamellae were rotated with respect to the scaffold longitudinal axis, equivalent transverse struts also shared complementary rotation, resulting in no struts lying parallel to the scaffold transverse plane and adding significant contribution to average cross section area. This was not the case in the orthogonal scaffold design, as transverse fibers contributed full fiber longitudinal cross section area to the average scaffold cross section area at those transverse ranges, resulting in approximately twice the overall scaffold average cross sectional area compared against the alternating design. Ultimate compressive strength differences reflected this as well, being on average 6.309 MPa for orthogonal specimens and 16.546 MPa for alternating specimens. However, the levels of load before conversion to stress for alternating scaffolds were still higher than orthogonal scaffolds, having more than twice the ultimate compressive strength.

To further investigate loadbearing differences between volumetrically similar scaffolds, finer analysis using SEM imaging contributes mechanistic fracture information. It was previously established that alternating specimens featured brittle strut fractures with no observable strut plastic deformation, while orthogonal specimens featured significant plastic deformation before undergoing eventual fracture of neighboring transverse struts. These differences in fracture mechanisms may also have been a result of variations in the geometric orientation of struts relative to the axis of applied loading. Plastic deformation, or buckling, is a common phenomenon of longitudinal axial compressive loading. However, alternating designs featured no strut longitudinal axial loading. Instead all the stress was applied under an angular shear regime, resulting in brittle fracture with transverse fracture surfaces typical of metal specimens. On a macroscopic scale, these mechanistic differences resulted in a general "crumpling" for alternating designs, wherein the failure was evenly distributed in the radial direction by strut fracture, while large plastic deformation characteristic of orthogonal designs led to an overall "buckling" of the specimens. These variations in the performance not only affected the scaffold mechanical properties, but also contributed to significant distinctions in the overall structure failure performance. General effects of these distinctions were characterized through scaffold deformation profiles quantifying uCT 3D scans. Buckling of orthogonal specimens can clearly be compared against crumpling of alternating specimens by observing changes in deformation over radial position for transverse sections over the length of the specimens. This is further evidence of the clear variation in failure performance for the two scaffold designs.

Previous research of failure mode fundamentals in fiber-reinforced composites (extrapolated to the fibrous lamellae organization of scaffold designs featured herein) established classification of fracture behaviors into distinct categories of transverse shear, lamina bending, and local buckling under compressive loading. In consideration of the fracture behaviors exhibited by SEM images (FIG. 7), distinct behaviors of alternating and orthogonal struts may be translated into these terms. In observation of fracture edges, interlaminar, and longitudinal cracks in partial lamina bundles demonstrated by alternating specimens, the mode of failure of this scaffold design may be classified as transverse shearing crushing mode. In the orthogonal specimens, SEM results exhibit severe lamina bending, while interlaminar parallel-to-fiber cracks propagate within several adjacent lamina, while other lamina bundles exhibit significant plastic bending deformation before fracture. These behaviors result in the categorization of the orthogonal scaffold design failure in the lamina bending crushing mode. These results thus contribute to an understanding of sustained scaffold crushing stress as a function of the ply angle, given that different conclusions for mechanical behavior may be reached for different ranges of ply angles investigated.

In the context of a loadbearing, bone tissue engineering application, these variations in failure performance may be significant in changing the scaffold interaction with the tissue-scaffold interface. Given the importance of surface contact in physiological regenerative processes including cell infiltration and surface remodeling, and applied stress in stimulating osteocyte activity, radial and longitudinal profiling of deformation under compressive loading for the cylindrical model evaluated, illustrates the clear significance of the geometric design. In consideration of the current geometric designs common to the field of SFF additive manufactured scaffolds, asymmetric plastic buckling of the orthogonal design featured in this study illustrates potential negative impacts upon the physiological interface. While it is acknowledged that compressive loading was performed in a free-standing context, and that future implant applications in a fully tissue-embedded context may result in different deformation behavior due to stress transference to surrounding tissue, it remains that excessive asymmetric stress transference and tissue stimulation may be inferior to symmetric performance given the goal of bone tissue engineering to reproduce the loading environment of native tissue. It is asserted that for larger scales of bone tissue engineering, especially in a heavier load-bearing context akin to normal bone functioning, the alternating biomimetic design presented herein offers superior performance in failure suitable for sustained biological interfacing.

Observing SEM images presented in FIG. 6 offers additional insight to possible biomimetic mechanical behavior arising from the biomimetic structural design for alternating specimens. Fibrous lamellae of bone tissue are known to contribute mechanical performance through crack bridging and fracture deflection, where microscopic structures assist in preventing exacerbation of tissue defects. A similar phenomenon was observed in FIGS. 6A and 6B, where fractures were highly varied in length and angle compared to the extensive, linear fractures observed in FIGS. 6C and 6D. It is contemplated that this behavior is a macroscopic scaling of crack bridging and fracture deflection behaviors observed in microscopic iterations of this lamellar rotated plywood structure, in that larger, continuous fractures were hindered in formation by the alternating design and varying strut orientation between different lamellae as well in adjacent struts within the same lamella. This presentation resulted in presentation of a more homogenous fractured outer surface texture, as well as contribution toward radially symmetric failure performance. Large, extensive fractures in orthogonal specimens were also correlated with severe plastic deformation in neighboring longitudinal struts, with both being characteristic of asymmetric failure performance.

Another notable characteristic of alternating specimen stress-strain relationships was the lack of a distinction between elastic and plastic regions of deformation. As exhibited in FIG. 3, the graduated, sloping curvatures of alternating trends translates to more homogenous behavior under compression than that of orthogonal specimens which featured two distinct regions of mechanical behavior. Smooth compressive behavior may be a significant contributor to replicating organic phase contributions to bone tissue behavior, given the composition of bone tissue featuring collagen fibers which inherently behave more similarly to a viscoelastic tissue model than the stress-strain behavior of metal alloys.

In all, significant changes were demonstrated in the mechanical performance for the biomimetic variation in scaffold design with one-way independent ANOVA p-scores less than 0.001 for elastic modulus, ultimate compressive strength, and less than 0.004 for strain at failure. Aside from mechanical parameters of performance, qualitative and quantitative analysis of failure mode and deformation also showed distinct behaviors of the two scaffold designs. Given the isolated variable of geometric design, it is anticipated that a similar principle will be applied to future investigations featuring scaffold material compositions more widely accepted as standards for orthopedic implantation applications, namely titanium and its alloys. Verification of similar significant implications of structural variation in a greater variety of materials will generate stronger support for the possibility of fine-tuning structural design for mechanical performance in specific loadbearing contexts. The biomimetic design utilized herein was generated from previous experimental data taken from the human bone samples. Full complexity of the elucidated native tissue structure may be more fully represented through more extensive design and fabrication for structures featuring higher numbers of lamellar angular periodic repetitions, as well as internal channel microstructure for more faithful replication of the osteonal and vascular structures in bone.

Aside from mechanical performance parameters, other behaviors exhibited by the rotated plywood design suggested possibility of scaling up microscopic organic tissue phenomenon in response to mechanical stimulation that may offer previously unconsidered benefits on a macroscopic scaffold level. Additional loading regimes including shear and flexure may warrant further investigation given the complex loading environment of the native bone tissue and orthopedic implants upon clinical implementation. However, from the evaluations performed, it is believed that the rotated plywood design in tissue engineering applications may offer significant improvement to mechanical performance on existing SFF additive manufacturing designs, and may also contribute to future macroscopic space-filling, load-bearing applications of synthetic bone tissue replacements. Given the necessity of introducing tissue-like behaviors on a macroscopic level to non-organic implants and scaffolds, the concept of biomimetic design inspired from the complex hierarchical structures of bone tissue may improve compatibility of implant and scaffold performance beyond numeric parameter considerations, but also in more complex, structural geometry influenced behaviors such as compressive deformation, stress distribution, and fracture propagation. It is believed this research to be especially compatible with research on material composition for orthopedic implants given the independence of scaffold structural design to structural composition, and that insights derived from structural biomimetic design may be applied to a variety of materials.

Conclusions

Using binder-jet 3D SFF fabrication, biomimetic structural motifs may be implemented in load-bearing, lamellar, porous bone scaffolds to replicate and scale up complex hierarchical mechanical responses observed in natural tissues. Utilizing the rotated plywood design, deformation and buckling under compressive loading may be distributed evenly in the radial direction for superior interface with the surrounding physiological microenvironment in the context of implantation. Distinct changes in the mechanical performance from the elastic to plastic deformation regime transition may also be reduced and smoothed to a single regime as another result of crumpling scaffold behavior introduced by rotated plywood design. Mechanical performance parameters (including ultimate compressive strength and elastic modulus) may be greatly enhanced for rotated plywood design scaffolds of approximately similar bulk scaffold volume and porosity of compared against a standardized geometric mesh design.

Implementation of a biomimetic rotated plywood design also introduced semblances of fracture crack deflection behavior between and within scaffold lamellae, also serving to homogenize stress distribution away from asymmetries of stress concentration found in the orthogonal mesh design. Control for structural effects on mechanical performance suggests that further validation of design significance is possible for a wider range of scaffold materials. Quantitative variation on biomimetic design parameters for more specific control over aspects of mechanical performance remains an area of future investigation with the goal of creating scaffolds customized for specific stress-response behaviors in various dynamic loading regimes.

Whereas particular embodiments of the invention have been described herein for purposes of illustration, it will be evident to those skilled in the art that numerous variations of the details may be made without departing from the invention.

The invention claimed is:

1. A method of preparing a biomimetic scaffold, comprising:

performing a structural imaging analysis of natural bone tissue comprising a rotated or an alternated plywood lamellar structure;

employing data from the structural imaging analysis to specify design parameters of the biomimetic scaffold and to determine angular displacement of lamella in the rotated or alternated plywood lamellar structure;

obtaining a scaffold material comprising a material selected from the group consisting of metal, metal alloy, polymer, ceramic, and composites and blends thereof;

conducting an additive manufacturing process, comprising:
forming the scaffold material into a plurality of layers;
stacking the plurality of layers; and
aligning the plurality of layers; and rotating or alternating one or more of the plurality of layers to achieve an overall trend that mimics the angular displacement of lamella in the rotated plywood lamellar structure of the natural bone tissue.

2. The method of claim 1, wherein the scaffold material exhibits one or more properties selected from the group consisting of biodegradable, bioresorbable, bioabsorbable, biocompatible, bioinert, and bioactive.

3. The method of claim 1, wherein the structural imaging analysis is selected from the group of imaging modalities consisting of micro-diffraction image analysis, polarized light microscopy, confocal microscopy and SEM surface tomography, X-ray diffraction, X-ray diffraction tomography and X-ray micro computed tomography.

4. The method of claim 1, wherein the additive manufacturing process is selected from the group consisting of solid free-form layered manufacturing, fused deposition modeling, laser beam processing, electron beam processing, and combinations thereof.

5. The method of claim 1, wherein the additive manufacturing process is a 3-D printing process.

6. The method of claim 5, wherein the 3-D printing process comprises a binder-jet-3-DP apparatus.

7. A method of treating bone tissue defects in a human, comprising:
preparing a biomimetic scaffold, comprising:
performing a structural imaging analysis of natural bone tissue comprising a rotated or an alternated plywood lamellar structure;
employing data from the structural imaging analysis to specify design parameters of the biomimetic scaffold and to determine angular displacement of lamella in the rotated or alternated plywood lamellar structure;
obtaining a scaffold material comprising a material selected from the group consisting of biodegradable and non-biodegradable metal, metal alloy, polymer, ceramic, and composites and blends thereof;
conducting an additive manufacturing process, comprising:
forming the scaffold material into a plurality of layers;
stacking the plurality of layers; and
aligning the plurality of layers; and
rotating or alternating one or more of the plurality of layers to achieve an overall trend that mimics the angular displacement of lamella in the rotated plywood lamellar structure of the natural bone tissue; and
applying the biomimetic scaffold as a medical implantation device.

8. The method of claim 7, wherein the polymer is selected from the group consisting of polyhydroxy acid, polylactic acid, polyglycolic acid, polycaprolactone, and mixtures and blends thereof.

9. The method of claim 7, wherein the metal is selected from the group consisting of iron, iron alloys, titanium, titanium alloys, cobalt-chromium alloys, biodegradable magnesium, biodegradable magnesium alloys, and mixtures and blends thereof.

10. The method of claim 7 wherein the ceramic is selected from the group consisting of calcium phosphate, hydroxyapatite, tri-calcium phosphate, tetracalcium phosphate, and combinations of calcium phosphate cements and magnesium phosphate cements.

11. The method of claim 7, wherein the biomimetic scaffold is a cylinder shape.

* * * * *